(12) United States Patent
Schumacher

(10) Patent No.: US 11,298,223 B2
(45) Date of Patent: Apr. 12, 2022

(54) FOLDABLE ONE-WAY VALVE

(71) Applicant: GEONOVATION MEDICAL TECHNOLOGIES LTD., Netanya (IL)

(72) Inventor: Michaella Schumacher, Netanya (IL)

(73) Assignee: GEONOVATION MEDICAL TECHNOLOGIES LTD., Netanya (IL)

( * ) Notice: Subject to any disclaimer, the term of this patent is extended or adjusted under 35 U.S.C. 154(b) by 0 days.

(21) Appl. No.: 16/640,987

(22) PCT Filed: Aug. 15, 2018

(86) PCT No.: PCT/IL2018/050906
§ 371 (c)(1),
(2) Date: Feb. 21, 2020

(87) PCT Pub. No.: WO2019/038753
PCT Pub. Date: Feb. 28, 2019

(65) Prior Publication Data
US 2021/0121288 A1 Apr. 29, 2021

(30) Foreign Application Priority Data
Aug. 22, 2017 (IL) .......................................... 254099

(51) Int. Cl.
*A61F 2/24* (2006.01)

(52) U.S. Cl.
CPC .......... *A61F 2/2412* (2013.01); *A61F 2/2415* (2013.01); *A61F 2230/005* (2013.01)

(58) Field of Classification Search
CPC .............................. A61F 2/2415; A61F 2/2403
See application file for complete search history.

(56) References Cited

U.S. PATENT DOCUMENTS

| | | | |
|---|---|---|---|
| 3,548,417 A | 12/1970 | Kischer | |
| 6,283,994 B1 | 9/2001 | Moe et al. | |
| 8,591,575 B2 | 11/2013 | Cribier | |
| 2001/0002445 A1 | 5/2001 | Vesely | |
| 2002/0052651 A1 | 5/2002 | Myers et al. | |
| 2006/0009841 A1* | 1/2006 | McGuckin | A61F 2/2412 623/2.38 |
| 2011/0230956 A1 | 9/2011 | White | |
| 2012/0123529 A1 | 5/2012 | Levi et al. | |
| 2012/0185038 A1 | 7/2012 | Fish et al. | |
| 2013/0066418 A1 | 3/2013 | Matheny | |

FOREIGN PATENT DOCUMENTS

| | | |
|---|---|---|
| CN | 103237524 A | 8/2013 |
| CN | 103391756 A | 11/2013 |
| WO | 2014/100394 A1 | 6/2014 |
| WO | 2016/171340 A1 | 10/2016 |

* cited by examiner

*Primary Examiner* — Suba Ganesan
(74) *Attorney, Agent, or Firm* — Vorys, Sater, Seymour and Pease LLP; Anthony Venturino

(57) ABSTRACT

Provided is a foldable one-way valve prosthesis has an open state allowing a fluid to pass therethrough, and a closed state, preventing or at least reducing a reverse fluid flow therethrough. Leaflets are attached to each other along their common side edges with a possibility of pivoting relative to each other about the common side edge when the leaflets are folded along their folding lines causing the short section of the downstream edge to be angled with respect to the long section thereof, so as to bring the valve prosthesis into the closed state.

20 Claims, 5 Drawing Sheets

FOLDABLE ONE-WAY VALVE

TECHNOLOGICAL FIELD

The present invention relates to a one-way valve for any use, and particularly for use as a foldable valve prosthesis, for implantation in the body of a patient.

BACKGROUND

Foldable valve prostheses are well known in the art. Examples of such known valve prostheses are disclosed in U.S. Pat. Nos. 3,548,417, 8,591,575, and WO 2016/171340.

GENERAL DESCRIPTION

In accordance with the presently disclosed subject matter, there is provided a foldable one-way valve having an open state allowing a fluid to pass therethrough, and a closed state, preventing or at least reducing a reverse fluid flow therethrough. The valve prosthesis comprises:
  a closed contour base made of a relatively rigid material;
  a plurality of leaflets made of a relatively flexible material;
  each leaflet having:
  an upstream edge, at which the leaflet is at least indirectly attached to the base, the upstream edge extending between two upstream vertices;
  a downstream edge extending between two downstream vertices, the downstream edge having a folding point dividing the downstream edge into a long section extending between the folding point and a first of the downstream vertices, and a short section extending between the folding point and a second of the downstream vertices;
  a pair of side edges oriented transversely to the upstream and downstream edges, each side edge extending between opposite upstream and downstream vertices of the respective upstream and downstream edges; and
  a folding line extending between the folding point and a point on the upstream edge constituted by or disposed adjacent to the upstream vertex of the side edge, whose downstream vertex is the first downstream vertex.

The above valve can be used for any application, though a specific example disclosed herein is its use as a one-way valve prosthesis. Examples of other uses are valves for medical purposes other than prostheses such as in infusion pipes, in hearing aid devices, or for industrial purposes such as in installation or plumbing.

The leaflets are attached to each other along their common side edges with a possibility of pivoting relative to each other about the common side edge when the leaflets are folded along their folding lines causing the short section of the downstream edge to be angled with respect to the long section thereof, so as to bring the valve prosthesis into the closed state, in which all said folding lines form a central area, which is substantially smaller than the area bounded by the upstream edges.

With the structure of the prosthesis described above, and particularly, with the folding lines of its leaflets, desired closure thereof to prevent the backflow of the fluid, can be facilitated without requiring an unduly complicated assembly.

The upstream edge of the foldable one-way valve prosthesis can have a constant form in both the open and closed states of the prosthesis and it can have any appropriate shape. The downstream edge can also have any appropriate shape and it can be parallel to the upstream edge in the open state of the valve prosthesis. For example, both the upstream and downstream edges can be straight in said open state, whilst in the closed state only the former edge can maintain its straight shape. The side edges of each leaflet can be oriented perpendicularly to the upstream and downstream edges in the open state of the valve prosthesis.

The leaflets can be sewn to each other along their common side edge or constitute parts of a unitary piece of material, with specifically formed common side edges therebetween.

The common side edges and/or the folding lines can each be associated with a rib made of a flexible material at least indirectly attached thereto. In addition or alternatively, the common side edges and/or the folding lines can have strengthening stitches therealong.

The folding line can each divide its associated leaflet into a first section bounded by the folding line, the long edge section and the side edge having the first downstream vertex, and a second section bounded by the folding line, the short edge section, the side edge having the second downstream vertex and the upstream edge. The first section can be configured to fold over the second section to partially overlap it in the closed state.

The number of leaflets can be any appropriate, more particularly it can be more than two, still more particularly, between four to eight.

The base of the prosthesis can have any regular shape, e.g. it can be circular or polygonal.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

FIGS. 1 to 3C illustrate one example of a foldable one-way valve prosthesis 1, which has an open state (shown in FIG. 1) allowing a fluid to pass therethrough, a closed state (shown in FIGS. 2A to 2C) preventing or at least essentially reducing a reverse fluid flow therethrough, and an intermediate state (shown in FIGS. 3A to 3C), in which some of the fluid can pass through the valve prosthesis.

The foldable one-way valve prosthesis can be transplanted in the cardiovascular system of a human or non-human. In one example, it can be transplanted in the heart in order to functionally replace one of the pulmonary, tricuspid, mitral or aortic valves. The foldable one-way valve prosthesis can be also transplanted in other body channels, such as veins, or in organs. The prosthesis can also be transplanted in another prosthesis of the same kind, e.g. in case of malfunction of the latter prosthesis.

Figure 2A:
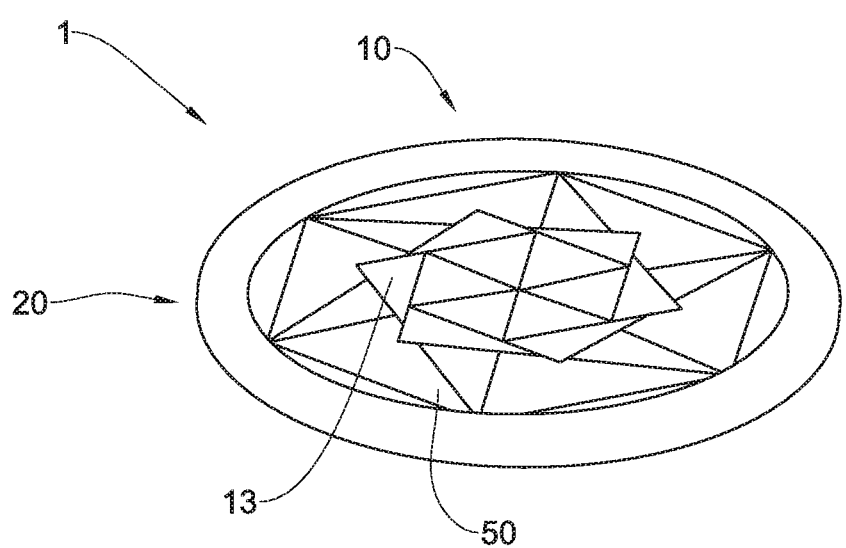
FIG. 2A is a perspective view of the valve prosthesis shown in FIG. 1 in its closed state.
Figure 2B:
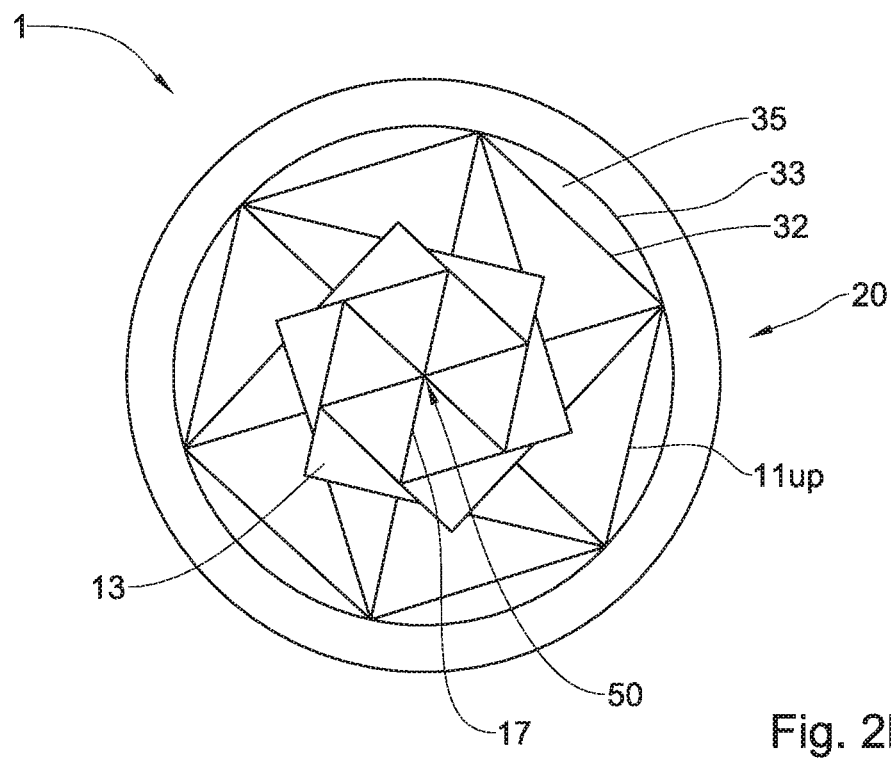
FIG. 2B is a top view of the valve prosthesis shown in FIG. 2A.
Figure 2C:
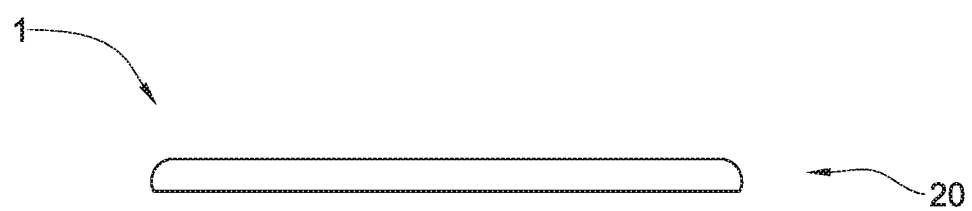
FIG. 2C is a side of the valve prosthesis shown in FIG. 2A.

The valve prosthesis is normally closed as shown in FIGS. 2A to 2C, and it becomes open in accordance with corresponding changes in the heart when the systole part of the cardiac cycle is followed by the diastole part of this cycle.

The valve prosthesis 1 comprises a foldable valve body 10 of a generally sleeve-like shape with an upstream end $10_u$ and a downstream end $10_d$, and a base 20, to which the valve body is securely attached at its upstream end $10_u$. As seen in FIGS. 1 and 2A to 2C, the valve body has open and closed states defining the respective open and closed states of the valve prosthesis.

The foldable valve body 10 comprises a plurality of leaflets 11 made of a relatively flexible material compared with that of the base 20. This material should be durable to repetition stresses associated with the folding of the valve body, on the one hand, and the need to be impermeable to fluids, on the other hand. One example of such material is a bovine or porcine pericardium. Alternatively, the leaflets can be made of synthetic tissue replacement material such as PTFE.

Figure 1:
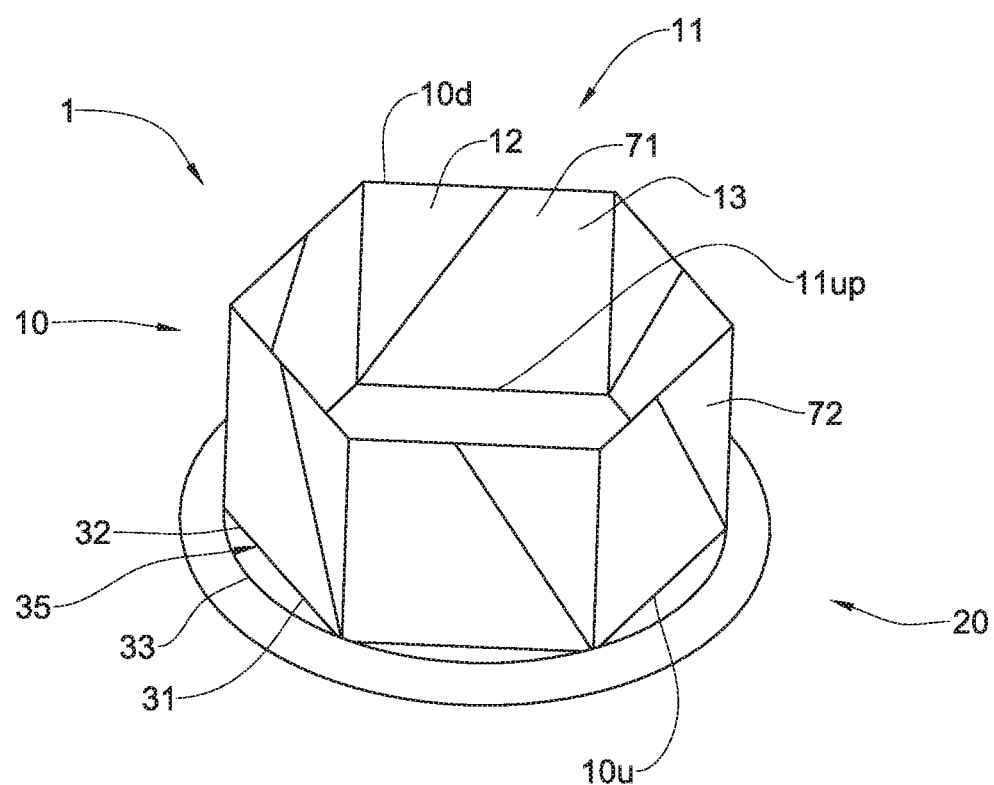
FIG. 1 is a perspective view of a valve prosthesis in its open state, according to one embodiment of the presently disclosed subject matter.

The valve prosthesis 1 can further comprise an attachment skirt, e.g. such as a skirt 30, as seen in FIG. 1, via which the valve body can be sealingly attached to the base. The skirt 30 can be made of the same material as the leaflets 11.

In general, the valve body 10 can comprise any number of leaflets 11. In the present example shown in FIGS. 1 to 3C, the valve body 10 comprises six leaflets 11.

Each leaflet 11 comprises an upstream edge $11_{up}$ adjacent the base 20, a downstream edge $11_{down}$ remote from the base 20 and a pair of side edges 15, 16 extending therebetween. The upstream edge $11_{up}$ meets the side edges 15 and 16 at two upstream vertices $15_u$ and $16_u$, and the downstream edge $11_{down}$ meets the side edges 15 and 16 at two downstream vertices $15_d$ and $16_d$. The upstream vertices of all the leaflets all lie in an imaginary base plane BP, which will hereinafter be used as a reference for describing orientation of the edges of the leaflets in different states of the valve body.

Figure 3A:
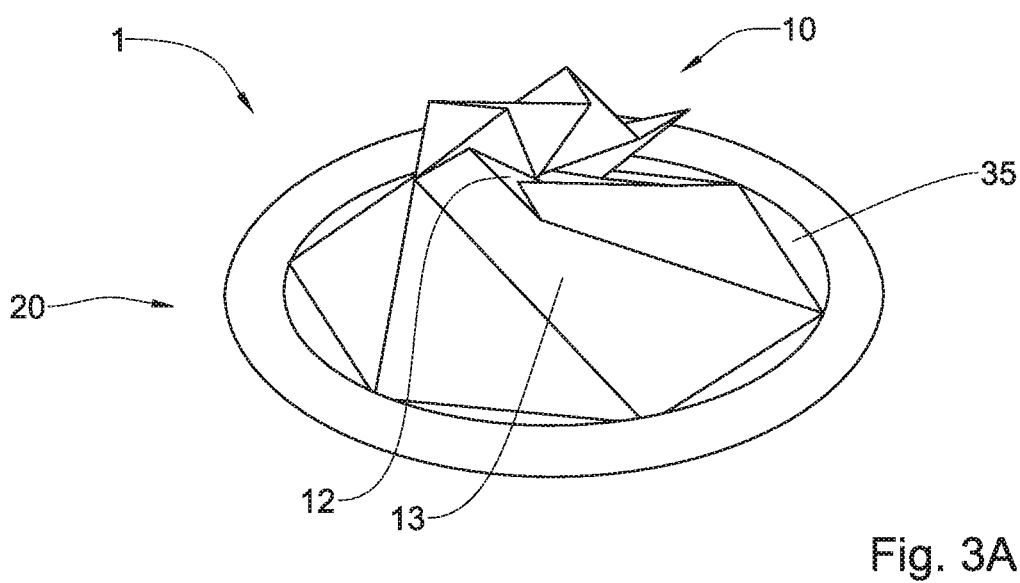
FIG. 3A is a perspective view of the valve prosthesis shown in FIG. 1 in its intermediate state.
Figure 3B:
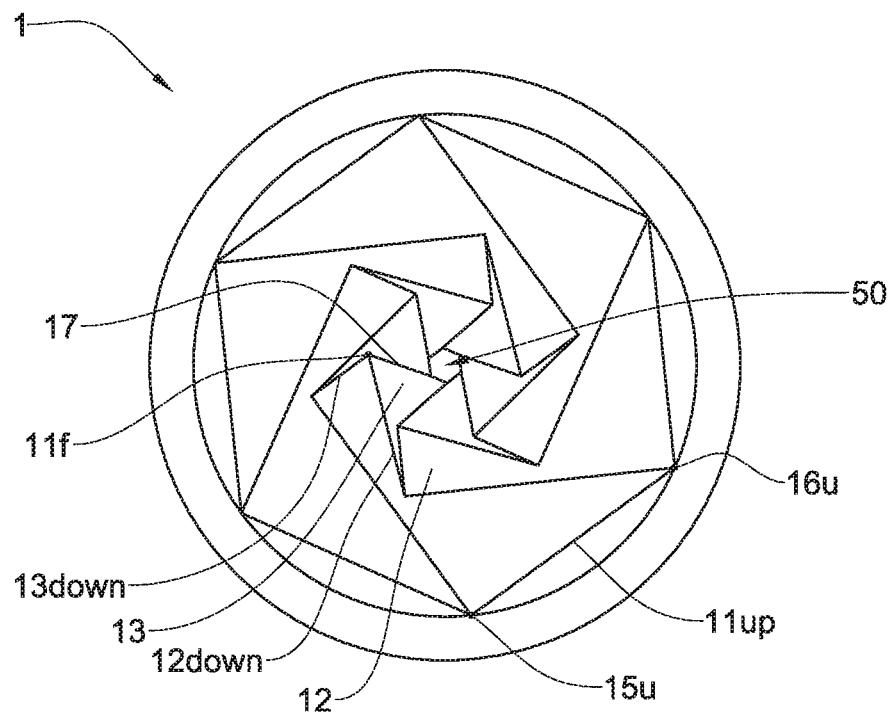
FIG. 3B is a top view of the valve prosthesis shown in FIG. 3A.
Figure 3C:
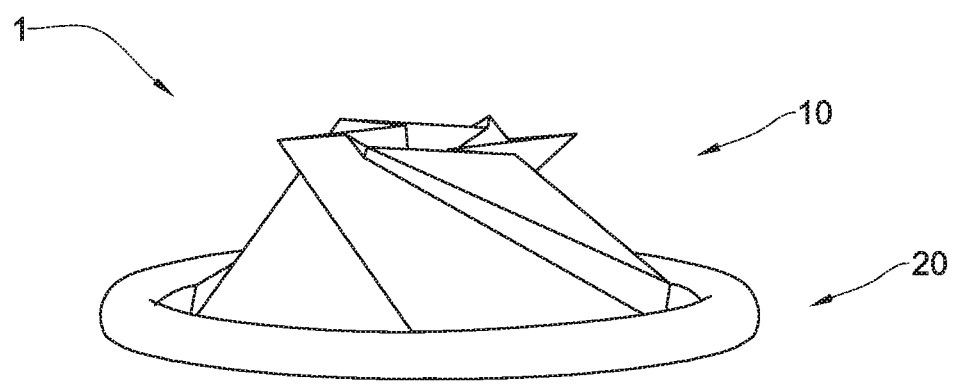
FIG. 3C is a perspective side of the valve prosthesis shown in FIG. 3A.

In general, each leaflet 11 can be attached to the base 20 directly or indirectly at the upstream edge $11_{up}$ thereof so as to allow it to stay in the same position relative to the base plane BP, and have different parts of at least a majority of the upstream edge, aligned in the same direction, both in the open and closed states of the valve body. In the present example, the upstream edge $11_{up}$ of each leaflet 11 is attached to the base 20 via the skirt 30 by any suitable means, e.g. by sewing or bonding, so that all its parts generally extend along a single straight line both in the open and closed states of the valve body, as seen in FIGS. 1 and 2B, as well as in the intermediate position as seen in FIG. 3B.

The downstream edge $11_{down}$ can generally be configured to change its position relative to the base plane BP and/or the direction, along which its different parts extend. More particularly, the downstream edge $11_{down}$ can change both its position relative to the base plane BP so that it is disposed closer thereto in the closed state of the valve body than in its open state, and the direction, along which it different parts extend so that, in the open state of the valve body, these parts have a mutual orientation different from that in the closed state of the body. FIGS. 1, 2A and 2B, illustrate this for the valve prosthesis of the present example, and particularly show that, whilst the downstream edge $11_{down}$ extends along a single line, which is straight in the open state of the valve body, this line becomes broken in the closed state of the valve body dividing the downstream edge $11_{down}$ into two parts, which extend along different lines angled to each other.

Still more particularly, in the present example, the downstream edge $11_{down}$ has a folding point $11_f$ dividing the downstream edge $11_{down}$ into a long section $12_{down}$ extending between the folding point $11_f$ and a first of the downstream vertices $16_d$, and a short section $13_{down}$ extending between the folding point $11_f$ and a second of the downstream vertices $15_d$. In the open state of the valve body, the long section $12_{down}$ and the short section $13_{down}$ are aligned along a single straight line, whilst in the closed state of the valve body, the short section $13_{down}$ is angled with respect to the long section $12_{down}$. The lengths of the short and long sections affect the extent of the closure of the valve body, so that in order to achieve the maximal closure, the long section should be essentially longer than the short section. For example, the lengths of the short and long section can be respectively, between 5%-25% and 95%-75% of the length of the downstream edge $11_{down}$.

The side edges 15 and 16 can generally be configured to change their position relative to the base plane BP and/or the direction, along which these edges extend. As best seen in FIGS. 1 and 3B, in the present example each side edge extends along a single straight line in both open and closed states of the valve body. However, its position relative to the base plane is changed so that in the open state of the valve body the side edges are parallel and form with the base plane BP a relatively large angle, e.g. 70-90°. In the closed state of the valve body, the side edges form a much smaller angle with the base plane BP, e.g. an angle not greater than 45°, more particularly, not greater than 30°, and they are oriented transversely to each other when seen in the top view of the valve prosthesis.

The length of the upstream and downstream edges generally depends on the number of leafs, and in case this number is more than two, this length can be equal or smaller than that of the side edges. In the latter case, i.e. when the upstream and downstream edges are shorter than the side edges, the ratio between their lengths can be between 0.5:1 and 0.8:1.

Each of the upstream and downstream edge can have any desired shape and, though in the present example, they are straight and parallel to each other in the open state of the valve body, this does not necessarily need to be the case. For example, they can both or one of them, e.g. the downstream edge can be curved. The same is correct with respect to the side edges.

In general, each leaflet 11 comprises a folding line 17, along which the leaflet is folded when the valve body is brought from its open to its closed state, and which has a downstream end constituted by the folding point $11_f$ of the downstream edge, and an upstream end $17_u$ on the upstream edge. The orientation of the folding line 17 can best be described relative to the side edges, with respect to which it is inclined so that its downstream end is disposed closer to one of the side edges than to the other side edge, whilst its upstream end is disposed closer to the latter side edge or is constituted by the upstream vertex of this side edge. In the present example, as best seen in FIG. 4A, the folding line 17 is inclined so that its downstream end constituted by the folding point $11_f$ is disposed closer to the side edge 15 than to the side edge 16, whilst its upstream end is constituted by the vertex $16_u$ of the side edge 16.

Figure 4A:
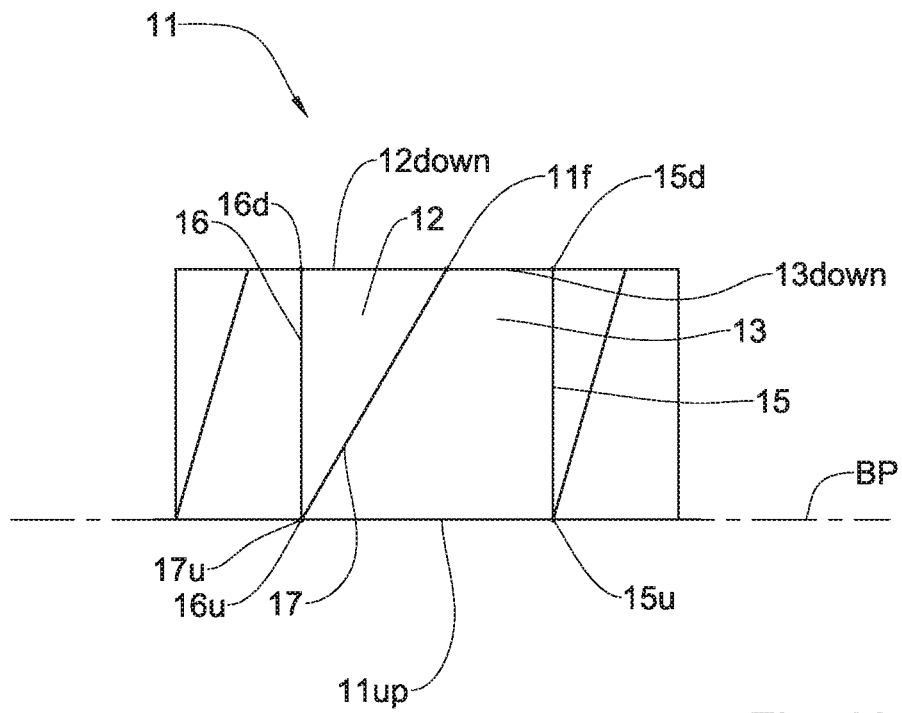
FIG. 4A is front view of a body of the valve prosthesis shown in FIG. 1, without its base.

In the present example, and as best illustrated in FIG. 4A, the folding line 17 divides each leaflet 11 into a first leaflet part 12, which has generally triangular shape, and is bounded by the folding line 17, the long edge section $12_{down}$ and the side edge 16, and a second leaflet part 13, which has a generally trapezoid shape and is bounded by the folding line 17, the short edge section $13_{down}$, the side edge 15.

In the closed state and through the intermediate state shown in FIGS. 2A-3C, the first leaflet part 12 overlies the second leaflet part 13 and partially overlaps therewith when seen in the top view of the valve. Consequently, as seen in FIG. 2C, when the first leaflet parts 12 of all the leaflets overlie the second leaflet parts 13 thereof, the valve body 10 can reach a substantially flat form in which its height over the base plane BP is essentially smaller than that in the open state of the valve body. For example, the former height can be not greater than 30%, more particularly, than 20% of the latter height.

In general, when the leaflets are folded along the folding lines 17 to bring the valve body into its closed state, the folding lines 17 can form therebetween a central area, which is substantially smaller than that bounded by the upstream edges $11_{up}$ of the valve body. In the present example, this area 50 is so tiny that it can be seen as a point through which all the folding lines 17 pass in the closed state of the valve body, as seen in the top view thereof shown in FIG. 2B.

Each leaflet can be in the form of a unitary piece of material with the folding line formed therein by any suitable means, e.g. by stitching, or it can be made of two separate pieces of the material connected along the folding line. In the present example, the first and second leaflet parts 12 and 13 constitute such pieces and they are sewn to each other along the folding line 17, to form the leaflet 11.

The leaflets 11 are attached to each other along their common side edges 15 and 16, with a possibility of pivoting relative to each other about these common side edges, prior to the attachment of the valve body 10 to the base 20. The leaflets 11 can be sewn to each other along their common side edge 15, 16 or constitute portions of a unitary piece of material, with the common side edges being formed therebetween, by any suitable means, such as for example, stitching.

Each leaflet 11 has a leaflet inner surface 71 and a leaflet outer surface 72. The leaflet inner surfaces 71 constitute an inner surface of the valve body of the valve prosthesis, which is configured to be in contact with the fluid which passes therethrough in the open state thereof.

Reverting to the attachment means in which the valve body 10 can be attached to the base 20, example of this is the skirt 30, which can be used as shown in FIG. 1. The skirt should be configured to be securely and sealingly attached to the base 20 at one end thereof and the valve body at another end. Thus, in general, the shape of the skirt should conform the shape of the base and its attachment location thereof.

Figure 4B:
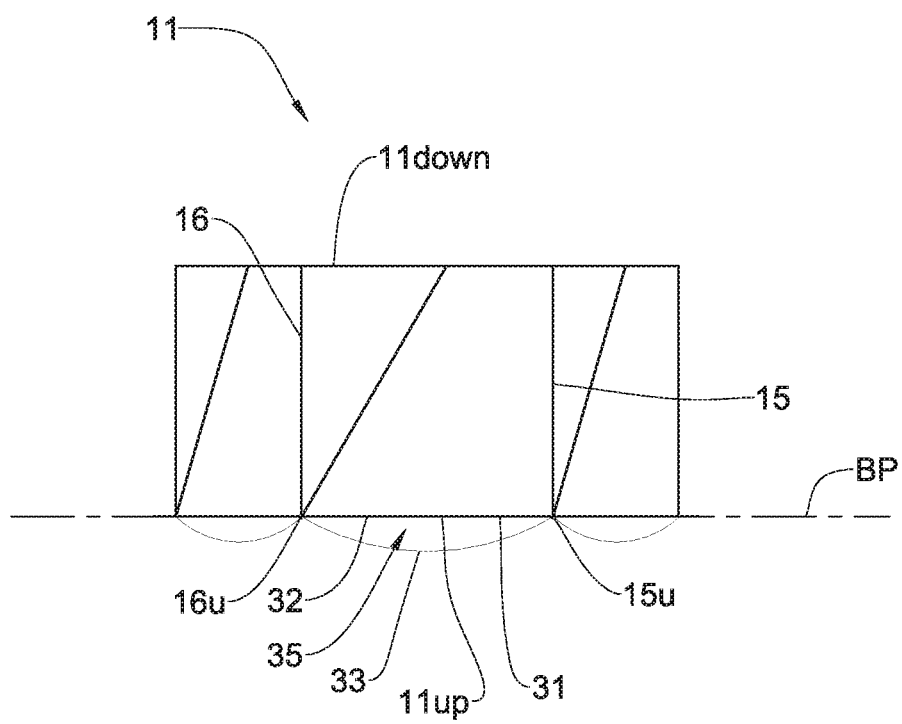
FIG. 4B is an illustration of the design of leaflets and skirts shown in FIG. 1.

In the present example, best seen in FIG. 4B, the skirt 30 comprises a plurality of skirt sectors 35 each integrally connected with the upstream edge of each leaflet $11_{up}$ so as to allow the leaflet' pivoting thereabout when the valve body changes its state from open to closed and vice versa. The skirt sectors 35 have arcuate shape of their lateral edges 33 which together form a circular circumference of the skirt 35, at which it is attached to the base. The skirt sections 35 and the leaflets 11 can be sewn together along their common edges. Alternatively, each pair of associated skirt section 35 and leaflet 11 can be made out of a unitary piece of a material, foldable along the upstream edge of the leaflet $11_{up}$. In a more particular example, all the leaflets 11 and the outer skirt sections 35 can be formed from a unitary piece of material, with the leaflets being connected to each other along their common side edges.

In another example, each of the skirt sectors can have a trapezoidal shape, which its first base is attached to the upstream edge of each leaflet $11_{up}$, and its opposite base is attached to the base. The trapezoidal skirt sectors are attached to each other along their common legs.

Figure 5A:
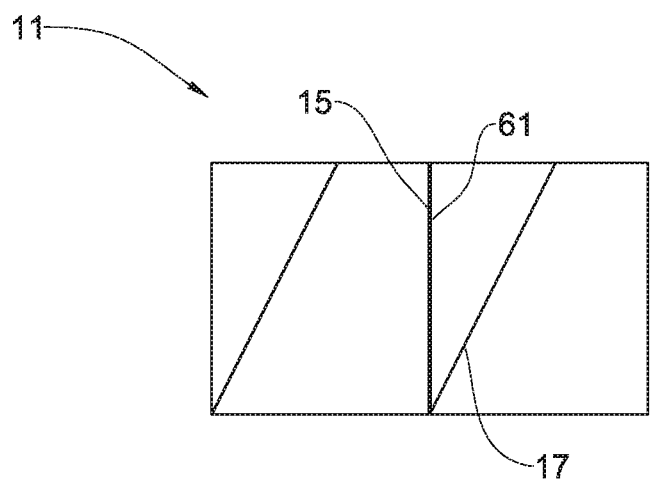
FIG. 5A-C illustrate the design of leaflets of the valve body of a valve prosthesis in its open state, according to alternative embodiments of the presently disclosed subject matter.
Figure 5B:
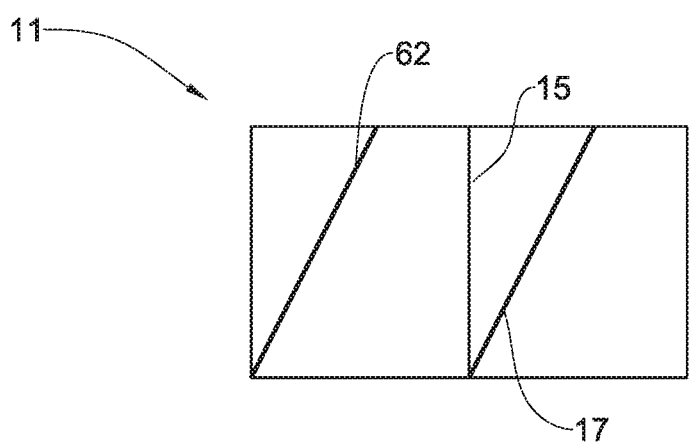
Figure 5C:
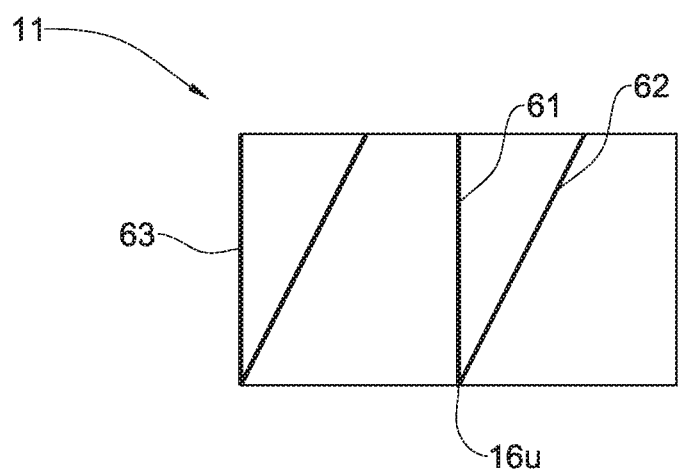

In order to better facilitate closure of the valve, and substantially prevent a back flow leakage, the valve body can further comprise a plurality of side edge stiffening ribs 61 each extending along at least a part of one of the common side edges 15, 16 of the leaflets, or along its entire length as shown, for example, in FIG. 5A. The valve body can comprise a plurality of folding line stiffening ribs 62 each extending along at least a part of one of the folding lines 17 as shown, for example, in FIG. 5B. In the example shown in FIG. 5C, the valve body of the valve prosthesis comprises both kinds of the stiffening ribs 61 and 62. The stiffening ribs 61 and 62 can be in the form of separate rods, or can be formed as a unitary V-shaped member. The ribs can be made of a material, such as e.g. casted biocompatible silicone, which is more flexible than the base 20 of the valve prosthesis but more rigid than the flexible material, from which the leaflets are made. The ribs 61 and/or 62 can be mounted to the leaflets by sewing means or can be held within corresponding suitable passages formed therein. Alternatively, the stiffening ribs can be in the form of thickening stitches formed along the side edges 15, 16, and/or the folding lines 17.

Reverting to the base 20, it is shown in the figures referred to above schematically only to illustrate that the valve body 10 needs a base to be mounted to.

In general, it should be understood that the base 20 can have any design including structure (multi- or single-component), shape (in transverse and longitudinal cross-sections) and material from which it is fully or partially made, suitable for use with the valve body 10 described above. For example, the base can have any form known to be used in heart valves including transcatheter valves, or stents.

Regarding the shape, the base can have a circular, oval or polygon transverse cross-section, and a rectangular or trapezoidal axial cross-section. The base illustrated in the present example has a ring-like shape.

Regarding the structure, the base can comprise a single component such as a frame. Alternatively, the base can comprise a frame which is at least partially wrapped thereabout with a cover in order to prevent leakage of majority of the fluid flow therethrough, and so the valve body can be attached thereto. In another example, the base can have the structure of a clamp, in which a first clamp portion, such as the above described frame, can be attached to the valve body, and a second clamp portion configured of being fixedly attached to the first clamp portion, post transplantation, in the transplantation site. Further, the second clamp portion can be configured of locking into position in the transplantation site without relative movement during systole and diastole.

Regarding the materials, the frame can be of a rigid material, so its form is constant. Alternatively, the frame can be made of a shape memory alloy, such as Nitinol, so that the valve prosthesis can be crimped while being delivered to the transplantation site. The cover can be made of a flexible material such as textile, or more particularly a woven polyester. In a particular example, the base is a stent graft which is comprised of a meshed frame with a cover made out of woven polyester. In another example, the base is a clamp having a first and a second clamp portions made of materials allowing the two to be crimped together or individually.

What is claimed is:

1. A foldable one-way valve prosthesis having an open state allowing a fluid to pass therethrough, and a closed state, preventing or at least reducing a reverse fluid flow therethrough, the valve prosthesis comprising:
    a closed contour base;
    a plurality of leaflets made of a relatively flexible material compared with that of the closed contour base;
    each leaflet having:
    an upstream edge at which it is at least indirectly attached to the base, the upstream edge extending between two upstream vertices;
    a downstream edge extending between two downstream vertices, the downstream edge having a folding point dividing the downstream edge into a long section extending between the folding point and a first of said downstream vertices, and a short section extending between the folding point and a second of said downstream vertices;
    a pair of side edges oriented transversely to the upstream and downstream edges, each side edge extending between opposite upstream and downstream vertices of the respective upstream and downstream edges; and
    a folding line extending between the folding point and a point on the upstream edge constituted by or disposed adjacent to the upstream vertex of the side edge, whose downstream vertex is said first downstream vertex;
    said leaflets being attached to each other along their common side edges with an ability of pivoting relative to each other about the common side edge when the leaflets are folded along their folding lines causing the short section of the downstream edge to be angled with respect to the long section thereof, so as to bring the valve prosthesis into said closed state, in which all said folding lines form a central area, which is substantially smaller than the area bounded by the upstream edges.

2. A foldable one-way valve prosthesis according to claim 1, wherein said upstream edge has a constant form in both said open and closed states.

3. A foldable one-way valve prosthesis according to claim 1, wherein said upstream edge is straight in both said open and closed states.

4. A foldable one-way valve prosthesis according to claim 1, wherein said downstream edge is parallel to the upstream edge in the open state of the valve prosthesis.

5. A foldable one-way valve prosthesis according to claim 1, wherein said downstream edge is straight.

6. A foldable one-way valve prosthesis according to claim 1, wherein said pair of side edges are oriented perpendicularly to the upstream and downstream edges in the open state of the valve prosthesis.

7. A foldable one-way valve prosthesis according to claim 1, wherein the leaflets are sewn to each other along their common side edge.

8. A foldable one-way valve prosthesis according to claim 1, wherein the leaflets constitute parts of a unitary piece of said material, with specifically formed common side edges therebetween.

9. A foldable one-way valve prosthesis according to claim 1, wherein each leaflet has a leaflet inner surface and a leaflet outer surface, and the leaflet inner surfaces constitute an inner surface of a circumferential wall of the valve prosthesis.

10. A foldable one-way valve prosthesis according to claim 9, wherein said circumferential side wall of the valve prosthesis has an inner surface which is in contact with said fluid in the open state.

11. A foldable one-way valve prosthesis according to claim 1, further comprising a plurality of ribs made of a flexible material, wherein each of said ribs is at least indirectly attached to one of said common side edges.

12. A foldable one-way valve prosthesis according to claim 1, wherein said folding line divides said each leaflet to a first section bounded by the folding line, the long edge section and the side edge having said first downstream vertex, and to a second section bounded by the folding line, the short edge section, the side edge having said second downstream vertex and the upstream edge.

13. A foldable one-way valve prosthesis according to claim 12, wherein said first section folds over said second section to partially overlap it in the closed state.

14. A foldable one-way valve prosthesis according to claim 12, wherein said first and second sections are sewn to each other.

15. A foldable one-way valve prosthesis according to claim 12, further comprises stitches along said folding lines.

16. A foldable one-way valve prosthesis according to claim 1, further comprising a plurality of ribs made of flexible material, wherein each of said ribs is at least indirectly attached to one of said folding lines.

17. A foldable one-way valve prosthesis according to claim 1, wherein said leaflets are more than two in number.

18. A foldable one-way valve prosthesis according to claim 17, wherein said leaflets are four to eight in number.

19. A foldable one-way valve prosthesis according to claim 1, wherein the length of said short section is between 5% to 25% of the length of said downstream edge.

20. A foldable one-way valve prosthesis according to claim 1, wherein a ratio between lengths of the upstream edge and the side edge is between 0.5 and 0.8.

* * * * *